(12) United States Patent
Krebs (10) Patent No.: US 7,695,672 B2
(45) Date of Patent: Apr. 13, 2010

(54) METHOD AND APPARATUS FOR DISINFECTING A PRODUCT BY SURFACE TREATMENT THEREOF

(75) Inventor: Niels Krebs, Brondby (DK)

(73) Assignee: Force Technology, Brondby (DK)

( * ) Notice: Subject to any disclaimer, the term of this patent is extended or adjusted under 35 U.S.C. 154(b) by 1888 days.

(21) Appl. No.: 10/472,219

(22) PCT Filed: Mar. 27, 2002

(86) PCT No.: PCT/DK02/00211

§ 371 (c)(1),
(2), (4) Date: Sep. 18, 2003

(87) PCT Pub. No.: WO02/078751

PCT Pub. Date: Oct. 10, 2002

(65) Prior Publication Data

US 2004/0105779 A1 Jun. 3, 2004

(30) Foreign Application Priority Data

Mar. 28, 2001 (DK) ................................. 2001 00514

(51) Int. Cl.
*A61L 2/08* (2006.01)
*A61L 2/00* (2006.01)
*A62B 7/08* (2006.01)
*B06B 1/00* (2006.01)
*B08B 3/12* (2006.01)

(52) U.S. Cl. ............................... 422/20; 422/1; 422/26; 422/127; 422/128; 422/292; 422/295; 422/300; 422/305; 422/307; 134/1

(58) Field of Classification Search ...................... 422/1, 422/20, 26, 127–128, 292, 295, 300, 305, 422/307; 134/1
See application file for complete search history.

(56) References Cited

U.S. PATENT DOCUMENTS 3,829,015 A * 8/1974 Monro ........................ 239/425
3,849,195 A * 11/1974 Powell et al. .................. 134/1

(Continued)

FOREIGN PATENT DOCUMENTS

DE 198 60 290 12/1998

(Continued)

OTHER PUBLICATIONS

On-line definitions of supersonic and ultrasonic by Merriam-Webster.*

(Continued)

*Primary Examiner*—Jill Warden
*Assistant Examiner*—Monzer R Chorbaji
(74) *Attorney, Agent, or Firm*—Day Pitney LLP (57) ABSTRACT

A method and an apparatus in form of a disinfecting apparatus comprising a steam device for combating germs on the surface of products, in particular of food products. The apparatus employs a combination of steam and ultrasound to kill germs on the surface of a product which is conveyed past the steam device. Pressurized steam is fed through a steam passage to an opening conveying the steam to a cavity, in which the steam is made to oscillate at a ultrasonic frequency. The oscillations in the steam prevent the steam from heating the products excessively, while germs presents on the surface of the products are heated and killed.

8 Claims, 6 Drawing Sheets

U.S. PATENT DOCUMENTS 4,347,983 A    9/1982   Bodai et al.
4,710,233 A *  12/1987  Hohmann et al. ............ 205/701
5,144,144 A *  9/1992   Borovsky .............. 250/455.11
5,403,555 A *  4/1995   Steinhauser et al. ......... 422/128
6,116,858 A *  9/2000   Narabayashi ................ 417/54

FOREIGN PATENT DOCUMENTS

| | | |
|---|---|---|
| EP | 0 711 566 | 5/1996 |
| FR | 2 811 574 | 7/2000 |
| JP | 0714 3999 A | 11/1993 |
| RU | 2119801 C1 | 10/1998 |
| RU | 2161560 C2 | 1/2001 |
| SU | 577051 | 10/1977 |
| SU | 1050711 A | 10/1983 |
| SU | 2000058 | 12/1990 |
| WO | 00/01255 | 1/2000 |

OTHER PUBLICATIONS

On-line definitions of supersonic and ultrasonic by Websters.*

* cited by examiner

METHOD AND APPARATUS FOR DISINFECTING A PRODUCT BY SURFACE TREATMENT THEREOF

TECHNICAL FIELD

The invention relates to a method for disinfecting a product by surface treatment thereof, steam of a liquid, preferably aqueous steam, and sound, preferably ultrasound, being discharged to the surface of the product.

When processing and subsequent packing food products it is desirable to kill germs, such as spores, micro-organisms and the like present on the surface of the food products and on other firm surfaces. It is known to heat-treat food to kill germs. However such a heat treatment usually causes unwanted changes in the flavour and texture of the treated food and may at worst spoil the food. It is also known to remove impurities from the surface of a product by ultrasonic treatment thereof.

BACKGROUND ART

Japanese published specification No JP-0714 3999A discloses a sterilization apparatus, in which the instruments to be sterilized first are exposed to ultrasound and then autoclaved by means of high-pressure steam, and finally irradiated with ultraviolet light. This principle is, however, not suitable for the treatment of food inter alia due to the high temperatures used during the autoclave process.

Furthermore EP 0711566A1 discloses a method and an apparatus for degerminating dental instruments. The apparatus employs various principles for combatting germs, eg. treatment with jets of steam, hot air, ultrasound bath, electromagnetic radiation, etc. This apparatus is, however, not suitable for the treatment of food, as too high heat volumes are absorbed by the treated products in many of the proposed methods.

It is moreover known to heat the surface of for instances food products by means of steam to kill germs. However, in order to obtain the desired kill effect the outermost layers of the treated food are damaged as a result of excessive exposure.

It is further known from Russian patent No. 2000058 to sterilise fluid food products by means of a combination of steam and ultrasound. The food is fed to a container and a layer of the fluid food is formed by centrifugal force. Steam is supplied to the food from the inner surface of the container. The steam is injected through a plurality of nozzles, whereby ultrasonic oscillations are generated in the fluid food. During condensation of the steam a cavitation is formed. The use of this treatment method is limited for a number of reasons:—it is only suitable for fluid food products, —a centrifuge is required, and—water is supplied to the food due to the condensation of aqueous steam. This type of condensation is preferably avoided.

DESCRIPTION OF THE INVENTION

The object of the invention is to provide a method for the disinfection of a product and which is suitable for effectively killing germs on the surface of the product without inducing too much heat to the product.

A method of the above type is according to the invention characterised in that ultrasound is generated at the same time as the steam is discharged and made to oscillate at a frequency in the ultrasonic range at such a high acoustic pressure that the migration of the individual molecules exceeds the dimension of the bacteria or germs to be killed.

The ultrasound in the steam thus generates such high particle oscillations and particle velocities that the water molecules are alternately pumped to and from the surfaces of the products. As a result:
1. Power is supplied in form of steam;
2. The steam zone around the product is continuously removed to prevent condensation and insulation;
3. The natural microstructures in the surface do not prevent steam from reaching all germs.

This entails that
1. The surface of the product is heated to the temperature of the steam considerably faster than if the heat is conducted through the air zone surrounding the product.
2. Germs hidden in natural pockets and spores are heated without hardly affecting the food per se.

During treatment the temperature inside the product decreases as a function of the depth. This also applies to germs on the surface. In biological products the germs are typically several times smaller than the cell size of the product. This means that the germs reach a core temperature exceeding 70° C. at a time, at which the thermal gradient has only penetrated a few micrometers into the surface cells of the product.

When the treatment is subsequently completed, the amount of energy absorbed by the cells of the product distributes itself and results in a general heating of the product. Since the volume of the cells of the product exceeds the volume of germs, the total amount of heat induced during processing is very small and thus harmless to the products. The processing time is comparatively short, preferably only a few seconds.

In a particularly advantageous embodiment of the invention the ultrasound is generated by conducting steam through a ultrasound-generating device and causing the steam to oscillate at a frequency in the ultrasonic range at such a high acoustic pressure that the migration of the individual molecule exceeds the dimension of the bacteria or germs to be killed.

The ultrasound-generating device may for instance be formed of a jet stream and a cavity. Because the ultrasound is generated by the forced passage of steam through the device, the device may be considered to be a whistle.

The invention further relates to a disinfection apparatus for carrying out the method comprising a steam device for combatting germs on the surface of a solid product, especially of a solid food product, said steam device having at least one steam passage and an opening.

The disinfection apparatus is characterised in that a cavity is provided adjacent the opening, which in use is adapted to be supplied with a jet of aqueous steam under a comparatively high pressure through the steam passage, whereby the aqueous steam diffused from the opening is made to oscillate at a frequency determined by the cavity. As a result a particularly advantageous disinfection apparatus is obtained.

BRIEF DESCRIPTION OF THE DRAWINGS

The invention is described in greater detail below with reference to the accompanying drawings, in which.

BEST MODES FOR CARRYING OUT THE INVENTION

Figure 1:
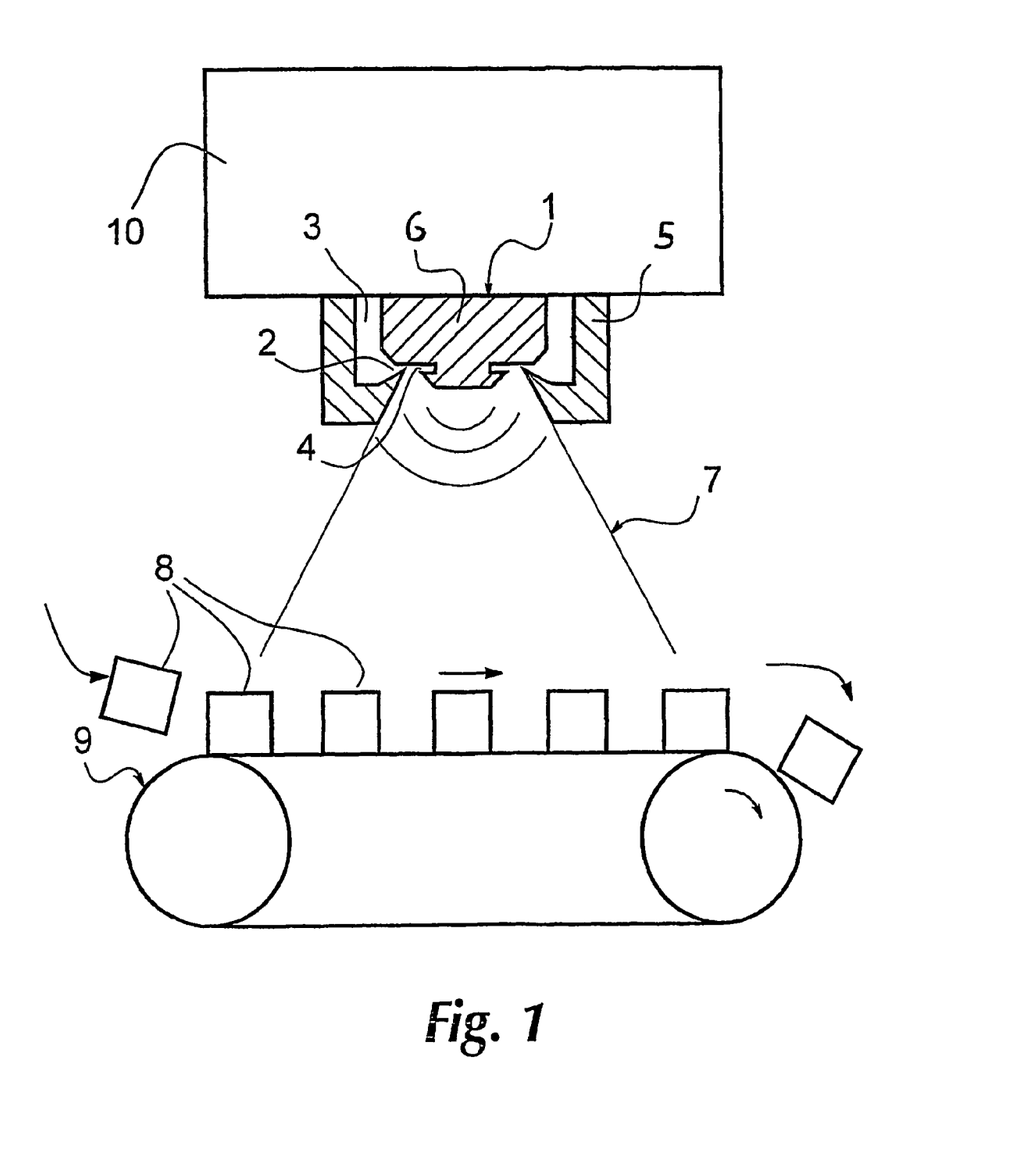
FIG. 1 shows the diffusion of a steam jet from a steam device of a disinfection apparatus according to the invention.

The disinfection apparatus shown in FIG. 1 for carrying out the method according to the invention comprises a steam device 1 shaped as a disc-shaped so-called disc jet comprising an outer part 5 and an inner part 6, which is displayed in a sectional view in the figure. Pressurized water is passed from a steam chamber 10 through a steam passage 3 defined by the outer part 5 and the inner part 6 to an opening 2, from which the steam is discharged in a jet towards a cavity 4 provided in the inner part 6. The steam may be made from distilled or demineralized water. If the steam pressure is sufficient high oscillations are generated in the steam fed to the cavity 4 at a frequency defined by the dimensions of the cavity 4. By adapting the dimensions of the cavity 4 for instance such that its acoustic natural frequency ranges between 20 kHz and 25 kHz, the steam device 1 generates acoustic oscillations from the opening 2 provided the steam pressure is sufficiently high. A further increase of the steam pressure does not change the frequency significantly, but the acoustic pressure delivered by the steam device 1 is heavily increased. A steam device of the type shown in FIG. 1 is able to generate ultrasonic acoustic pressures of up to 160 $dB_{SPL}$ at a steam pressure of about 4 atmospheres. The steam device 1 may be made from brass, aluminium or stainless steel in a suitable stainless material or in any other sufficiently hard material. The material merely has to withstand the acoustic pressure and temperature to which the steam device is subjected during use. The method of operation is also shown in FIG. 1, in which the diffused steam 7 is made to oscillate by the cavity 4. The diffused oscillating steam is directed towards a subjacent conveyor 9, whereon the products 8, eg. the food products, to be disinfected, are arranged. The products 8 are conveyed at a predetermined velocity corresponding to the desired disinfection degree. The emitted oscillating steam may optionally be used to disinfect seeds.

Figure 2:
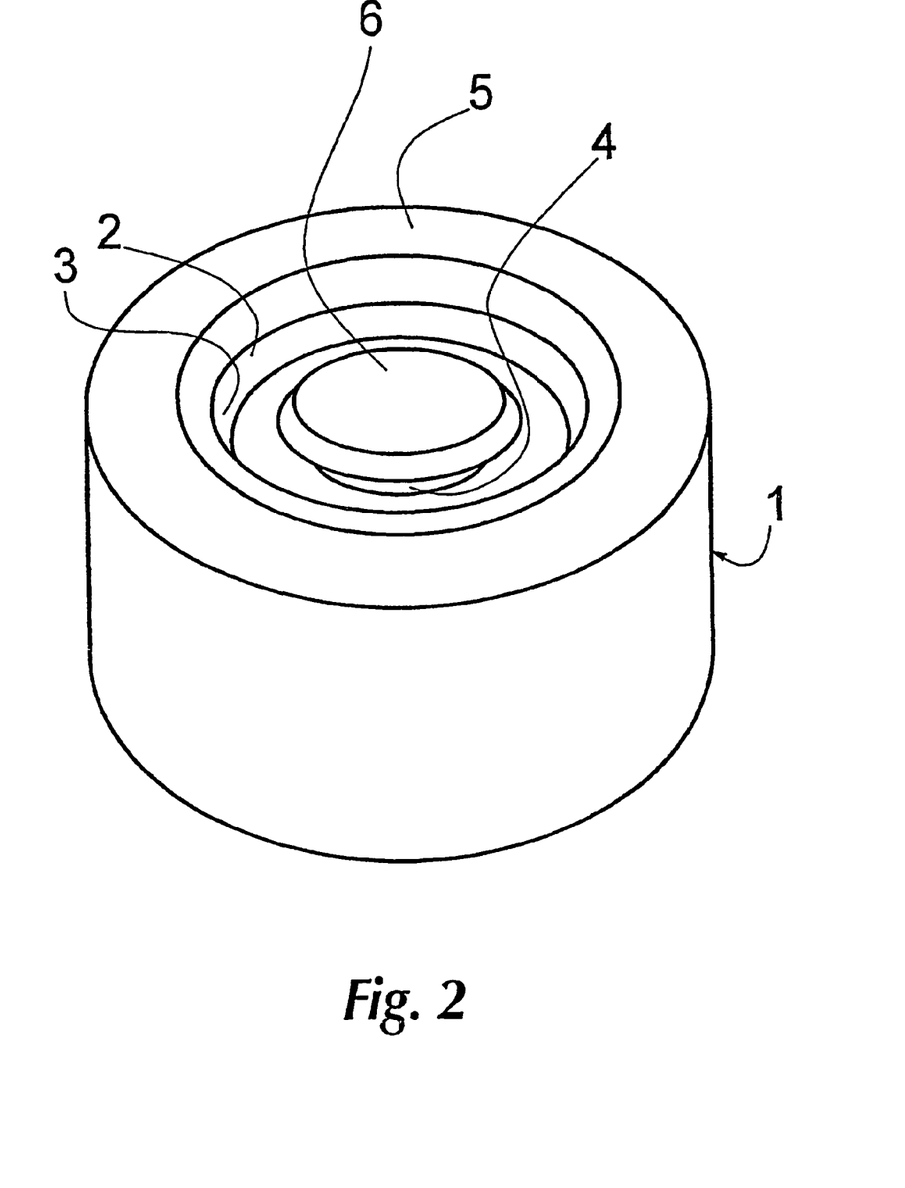
FIG. 2 shows an embodiment of a steam device in form of a disc-shaped disc jet.

An optional embodiment of a steam device according to the invention, ie. a so-called disc jet, is shown in FIG. 2. The steam device 1 comprises an annular outer part 5 and a cylindrical inner part 6, in which an annular cavity 4 is recessed. Through an annular steam passage 3 steam may be diffused to the annular opening 2 from which it may be conveyed to the cavity 4. The outer part 5 maybe adjustable in relation to the inner part 6, eg. by providing a thread or another adjusting device (not shown) in the bottom of the outer part 5, which further may comprise fastening means (not shown) for locking the outer part 5 in relation to the inner part 6, when the desired interval therebetween has been obtained. Advantageous dimensions of the steam device shown in FIG. 2 may be an external diameter of the outer part 5 of for instance 80 mm, an internal diameter of the rim of the opening 2 of about 22 mm, a diameter of the tip of the inner part 6, in which the cavity 4 is provided, of about 15 mm, and a cavity 4 having an internal diameter of about 10 mm and a width ranging from 1.5 to 2 mm. Such a steam device generates a frequency of about 19 kHz at a steam pressure of 4 atmospheres. The molecules of the steam are thus able to migrate up to 36 μm about 19,000 times per second at a maximum velocity of 4.5 m/s. These values are merely included to give an idea of the size and proportions of the steam device and by no means limit of the shown embodiment.

Figure 3:
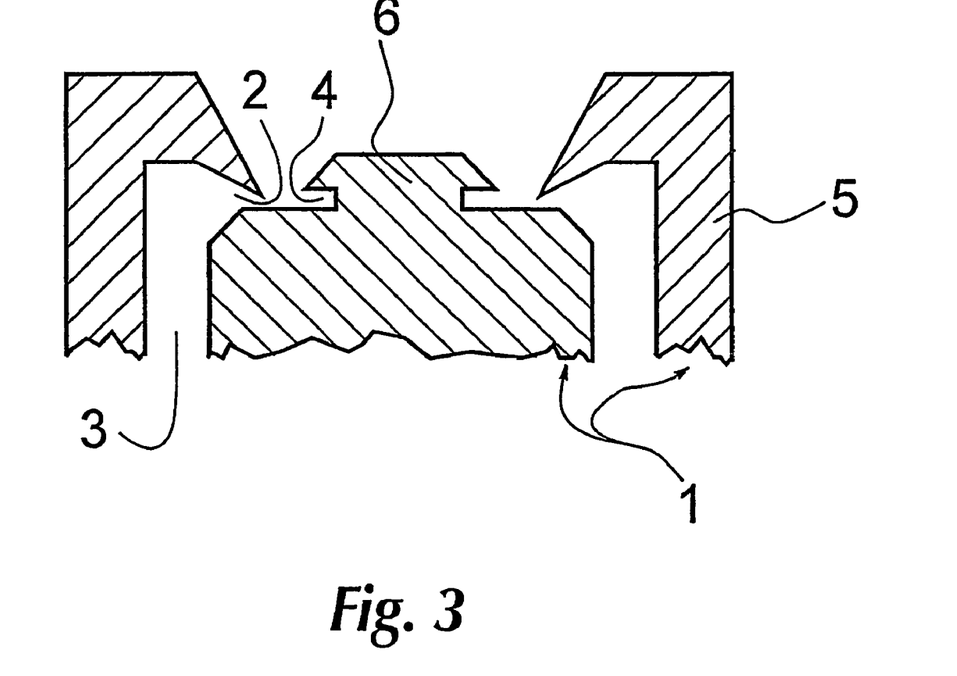
FIG. 3 is a sectional view along the diameter of the steam device in FIG. 2.

FIG. 3 is a sectional view of the steam device 1 in FIG. 2 so as to render the shape of the opening 2, the steam passage 3 and the cavity 4 more clearly. It is further apparent that the opening 2 is annular. The steam passage 3 and the opening 2 are defined by the substantially annular outer part 5 and the cylindrical inner part 6 arranged therein. The steam jet discharged from the opening 2 hits the substantially circumferential cavity 4 formed in the inner part 6, and then exits the steam device 1. As previously mentioned the outer part 5 defines the exterior of the steam passage 3 and is further bevelled at an angle of about 30° along the outer surface of its inner circumference forming the opening of the steam device, wherefrom the steam jet may expand when diffused. Jointly with a corresponding bevelling of about 60° on the inner surface of the inner circumference, the above bevelling forms an acute-angled circumferential edge defining the opening 2 externally. The inner part 6 has a bevelling of about 45° in its outer circumference facing the opening and internally defining the opening 2. The outer part 5 may be adjusted in relation to the inner part 6, whereby the pressure of the steam jet hitting the cavity 4 may be adjusted. The top of the inner part 6, in which the cavity 4 is recessed, is also bevelled at an angle of about 45° to allow the oscillating steam jet to expand at the opening of the steam device.

Figure 4:
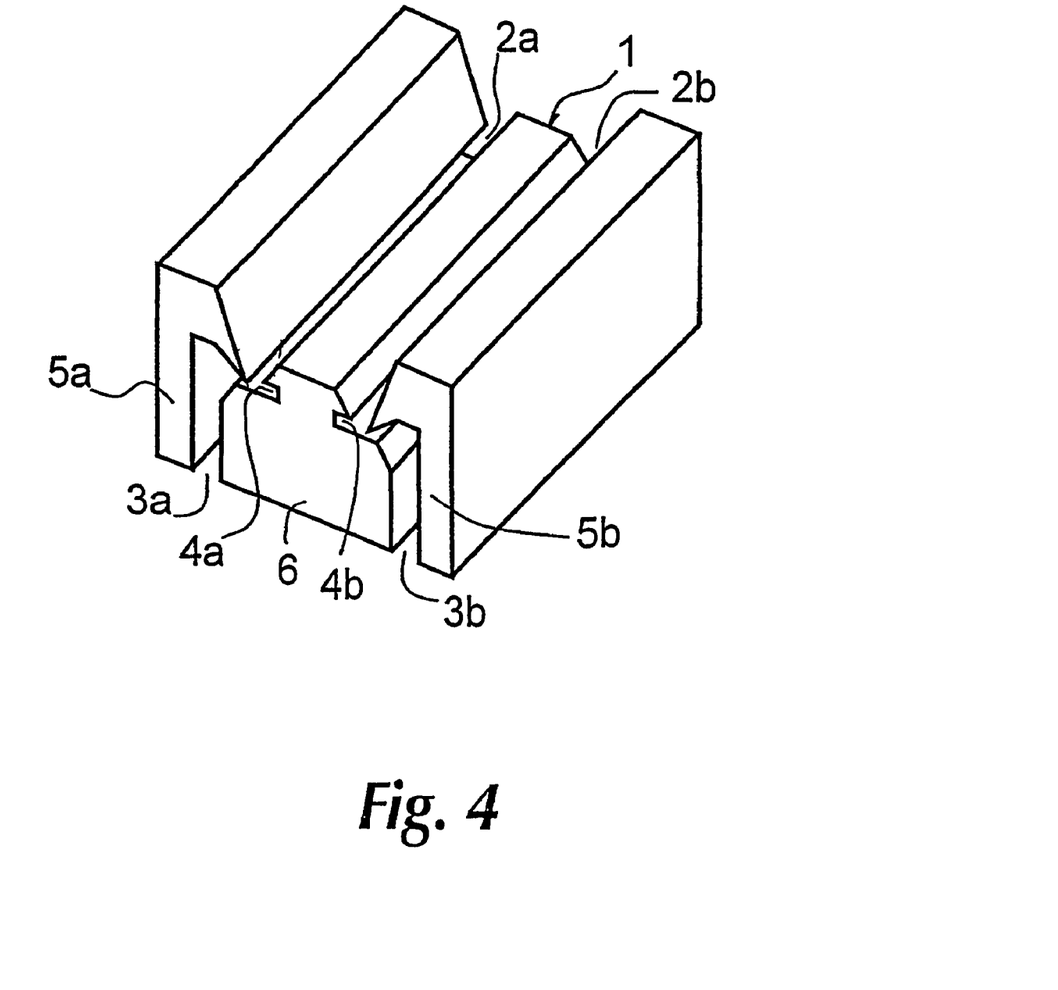
FIG. 4 shows a steam device shaped as a elongated body.

As an optional embodiment of the steam device of the disinfection apparatus an elongated, rail-shaped body 1 is shown in FIG. 4, said body being functionally equivalent with the embodiments shown in FIG. 1 and FIG. 2, respectively. In this embodiment the outer part comprises two separate rail-shaped portions 5a and 5b, which jointly with the rail-shaped inner part 6 form a steam device 1. Two steam passages 3a and 3b are provided between the two portions 5a and 5b of the outer part 5 and the inner part 6. Each of said steam passages has an opening 2a, 2b, respectively, conveying emitted steam from the steam passages 3a and 3b to two cavities 4a, 4b provided in the inner part 6. One advantage of this embodiment is that a rail-shaped body is able to coat a far larger surface area than a circular body. Another advantage of this embodiment is that the steam device may be made of extruded aluminium, whereby the cost of materials is reduced.

Figure 5:
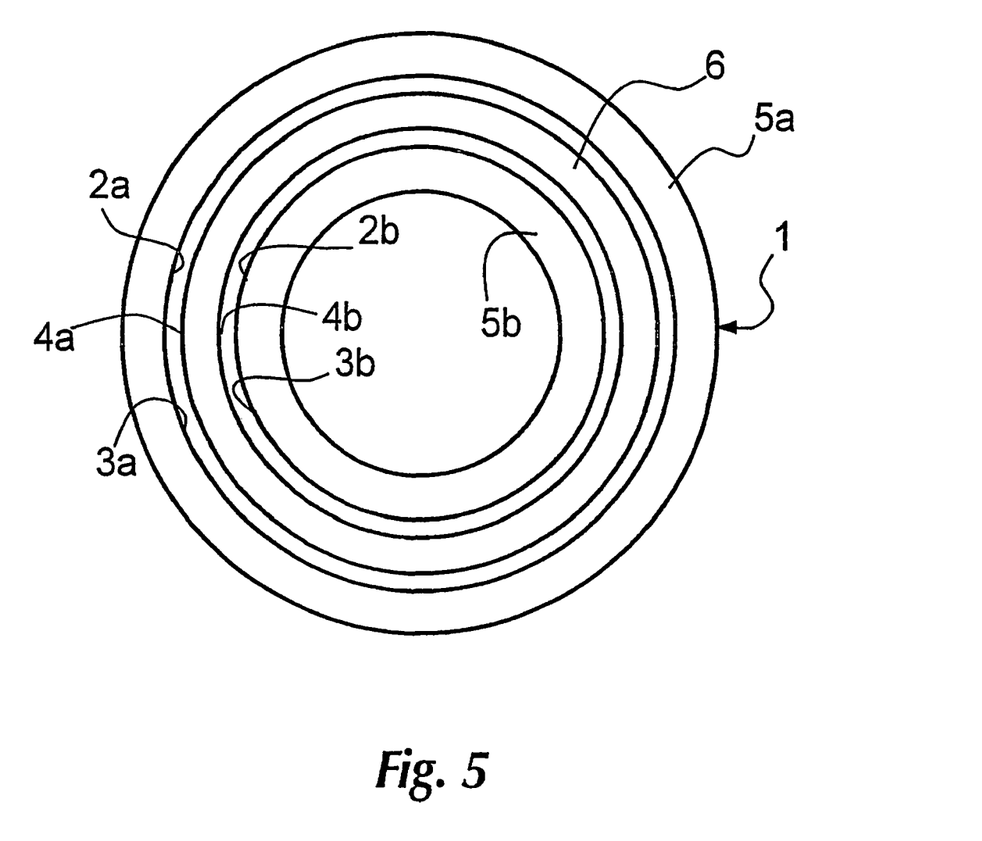
FIG. 5 shows a steam device of the same type as in FIG. 4 shaped as a closed curve.

The embodiment of the steam device shown in FIG. 4 does not have to be rectilinear. FIG. 5 shows a rail-shaped body 1 shaped as three circular, separate rings. The outer ring defines an outermost outer part 5a, the middle ring defines the inner part 6 and the inner ring defines an innermost outer part 5b. The three parts of the steam device jointly form a cross section as shown in the embodiment in FIG. 4, wherein two cavities 4a and 4b are provided in the inner part, and wherein the space between the outermost outer part 5a and the inner part 6 defines an outer steam passage 3a and an outer opening 2a, respectively, and the space between the inner part 6 and the innermost outer part 5b defines an inner steam passage 4b and an inner opening 2b, respectively. This embodiment of a steam device is able to coat a very large area at a time and thus treat the surface of large products such as food products, eg. whole cheeses, large vegetables or halved carcasses.

Figure 6:
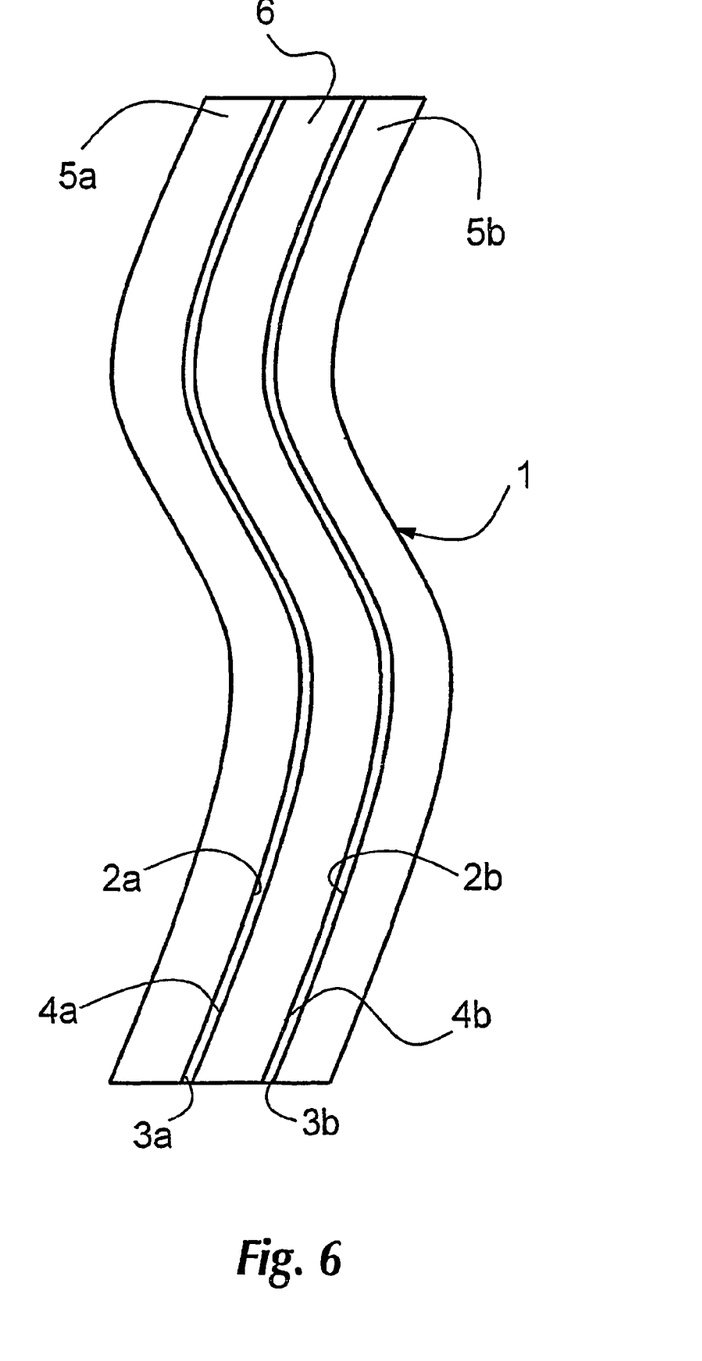
FIG. 6 shows a steam device of the same type as in FIG. 4 shaped as an open curve.

As shown in FIG. 6, it is also possible to form a steam device of this type as an open curve. In this embodiment the functional parts correspond to those shown in FIG. 4 and further details appear from this portion of the description for which reason reference is made thereto. A steam device shaped as an open curve is applicable where germs are to be eliminated from the surfaces of unusually shaped products. A system is envisaged, in which a plurality of steam devices shaped as different open curves are arranged in a disinfection apparatus according to the invention and used in a wide range of different applications.

In general the disinfection apparatus maybe used in connection with steam of a liquid, not necessarily aqueous steam. The disinfection apparatus may for instance be used in connection with alcohol. In the latter case various additives, optionally gaseous additives, may be added to the liquid.

Even though the disinfection apparatus according to the invention is described above with reference to the disinfection of the surface of food products, the invention is not restricted to this use. Examples of other possible applications of the invention include disinfection of surfaces of issue samples, disinfection of surgical instruments, surface activation of products in connection with chemical process technology and pharmaceutical industry or cleaning of food packagings prior to use thereof.

The invention may further be used in abattoirs, in food production in general, in operating theatres, in clean rooms, in biotechnological laboratories and livestock buildings, etc.

The apparatus is not necessarily stationary, but may also be a mobile unit.

The invention claimed is:

1. A method of disinfecting a solid product by the surface treatment thereof with steam, said method comprising:
   providing a supply of steam;
   oscillating said steam at an ultrasonic frequency such as to oscillate individual molecules of said steam supply at a sufficiently high acoustic pressure that said individual molecules of steam migrate a distance that exceeds the dimensions of any particles to be disinfected from said solid product;

discharging said oscillating steam onto said solid product and preventing condensation on a surface of said solid object by pumping water molecules of said steam alternatively toward and away from said surface of said solid product.

2. A method according to claim 1, wherein ultrasound is generated without inducing cavitation.

3. A method according to claim 1, wherein the simultaneous ultrasonic generation is provided by conveying steam through an ultrasound generating device causing the steam to oscillate at a frequency in the ultrasonic range.

4. Method according to claim 3, wherein the ultrasound generating device is formed of a jet stream and a cavity.

5. Method according to claim 3, wherein the ultrasound generating device is formed of a whistle for generating steam and ultrasound.

6. Method according to claim 1 comprising a relatively short processing time.

7. A method according to claim 1 wherein said solid product is a food product.

8. The method in accordance with claim 1 wherein said oscillating steam is discharged onto said solid product at a subsonic velocity.

* * * * *